(12) United States Patent
Kim et al.

(10) Patent No.: US 9,903,856 B2
(45) Date of Patent: Feb. 27, 2018

(54) OPTICAL BIOSENSOR

(71) Applicants: KOREA UNIVERSITY RESEARCH AND BUSINESS FOUNDATION, Seoul (KR); GWANGJU INSTITUTE OF SCIENCE AND TECHNOLOGY, Gwangju (KR)

(72) Inventors: Jungbae Kim, Seoul (KR); Min-Gon Kim, Gwangju (KR); Hyou-Arm Joung, Gwangju (KR); Yongho Wee, Gyeonggi-do (KR)

(73) Assignees: KOREA UNIVERSITY RESEARCH AND BUSINESS FOUNDATION, Seoul (KR); GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 26 days.

(21) Appl. No.: 14/403,240

(22) PCT Filed: May 21, 2013

(86) PCT No.: PCT/KR2013/004435
§ 371 (c)(1),
(2) Date: Nov. 24, 2014

(87) PCT Pub. No.: WO2013/176458
PCT Pub. Date: Nov. 28, 2013

(65) Prior Publication Data
US 2015/0111228 A1 Apr. 23, 2015

(30) Foreign Application Priority Data
May 22, 2012 (KR) .................. 10-2012-0054343

(51) Int. Cl.
*G01N 33/52* (2006.01)
*G01N 21/78* (2006.01)
*C12Q 1/25* (2006.01)
*C12Q 1/26* (2006.01)

(52) U.S. Cl.
CPC ............. *G01N 33/52* (2013.01); *C12Q 1/25* (2013.01); *C12Q 1/26* (2013.01); *G01N 21/78* (2013.01)

(58) Field of Classification Search
None
See application file for complete search history.

(56) References Cited

U.S. PATENT DOCUMENTS

| 7,678,567 B2 | 3/2010 | Uematsu et al. |
| 2004/0214253 A1 | 10/2004 | Paek et al. |
| 2010/0175991 A1* | 7/2010 | Shimomura ........... C12Q 1/001 204/403.1 |
| 2013/0130284 A1 | 5/2013 | Kim et al. |

FOREIGN PATENT DOCUMENTS

| KR | 1020040093048 | 11/2004 |
| KR | 1006164260000 | 8/2006 |
| KR | 1020110033575 | 3/2011 |
| KR | 1020110128128 | 11/2011 |

OTHER PUBLICATIONS

Le Geoff et al., "Enhanced Colorimetric Detection on Porous Microarrays Using in Situ Substrate Production", Analytical Chemistry 2011, vol. 83, pp. 3610-3615).*
Kim, Moon Il, et al., "Crosslinked Enzyme Aggregates in Hierarchically-Ordered Mesoporous Silica: A Simple and Effective Method for Enzyme Stabilization;" Biotechnology and Bioengineering, Feb. 1, 2007, vol. 96, No. 2, pp. 210-218.

* cited by examiner

*Primary Examiner* — Renee Claytor
*Assistant Examiner* — Michelle F. Paguio Frising
(74) *Attorney, Agent, or Firm* — Hultquist, PLLC; Steven J. Hultquist

(57) ABSTRACT

The present disclosure provides an optical biosensor based on a complex including a porous support on a chip and enzyme(s) immobilized inside the pores of the porous support, and a method for preparing the same. Since the colored product does not flow out of the pores but is concentrated therein, the optical biosensor of the present disclosure has remarkably improved sensitivity. In addition, it is possible to carry out quantitative determination and qualitative analysis since color intensity increases with time.

22 Claims, 12 Drawing Sheets

[Fig. 1]
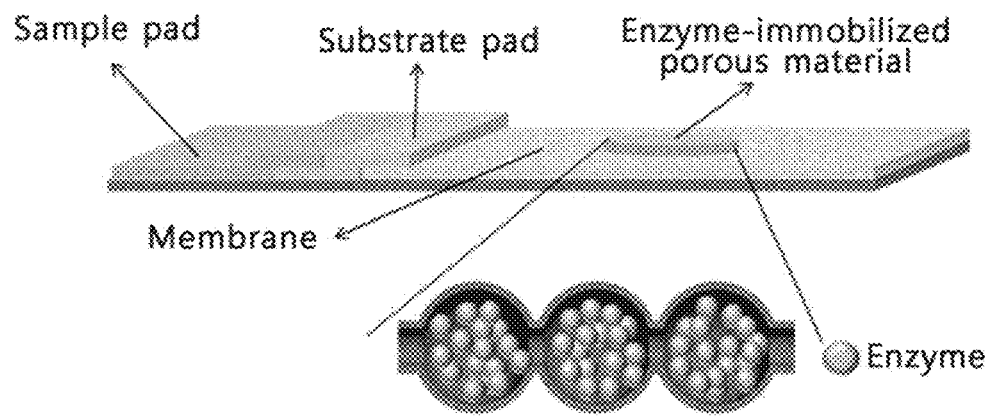
[Fig. 2]
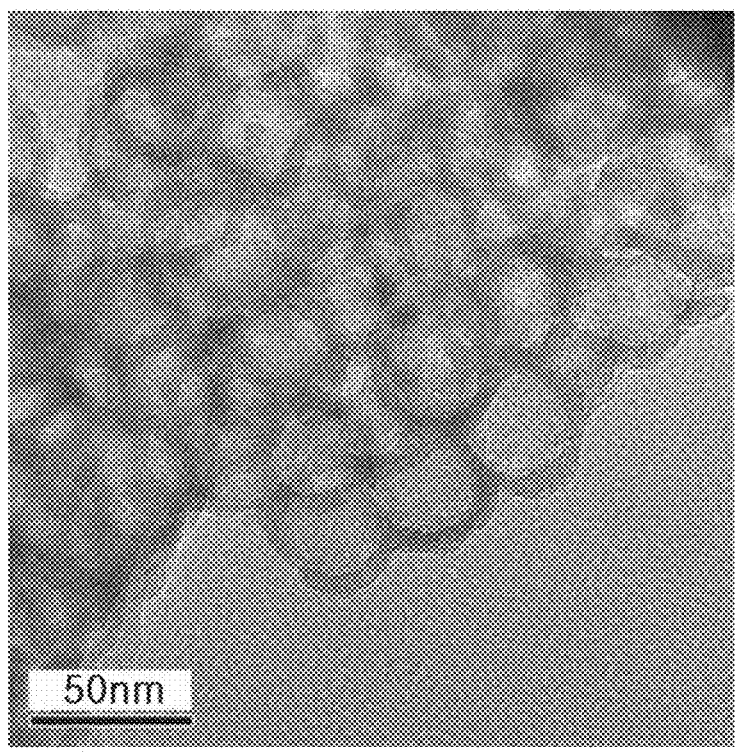

[Fig. 3a]
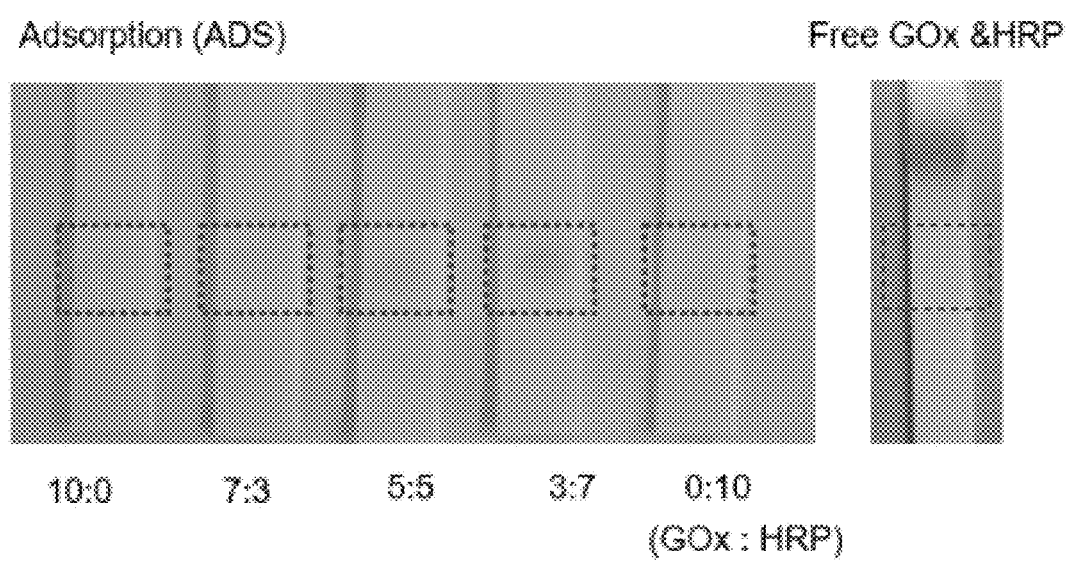

[Fig. 3b]
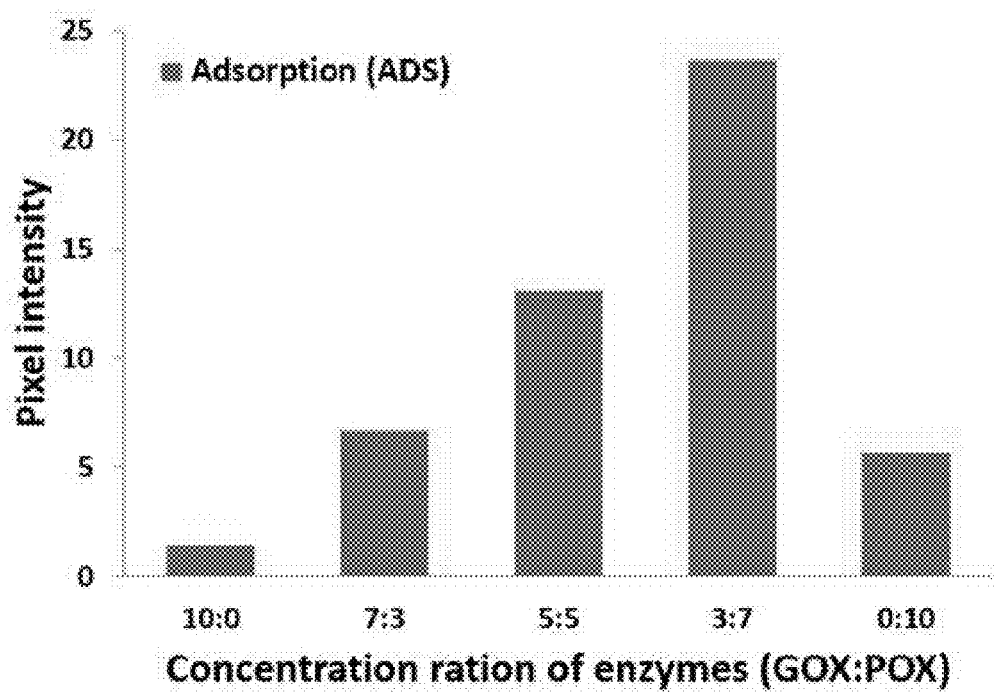

[Fig. 4]
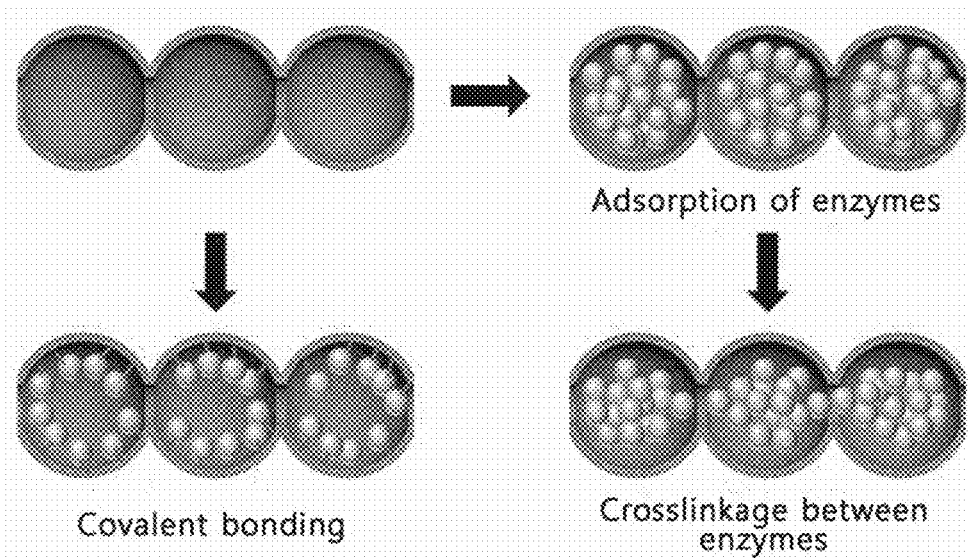
[Fig. 5]
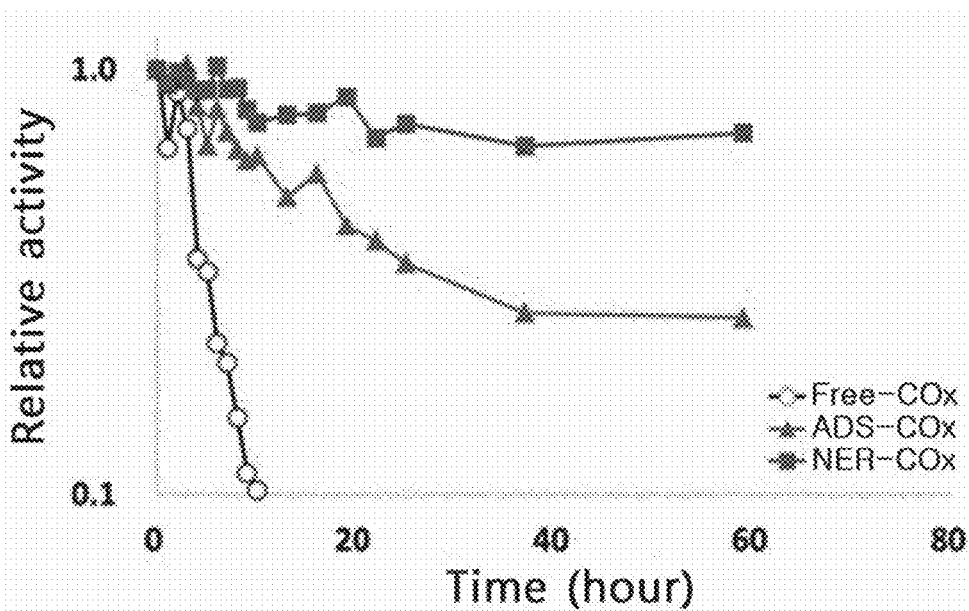

[Fig. 6a]
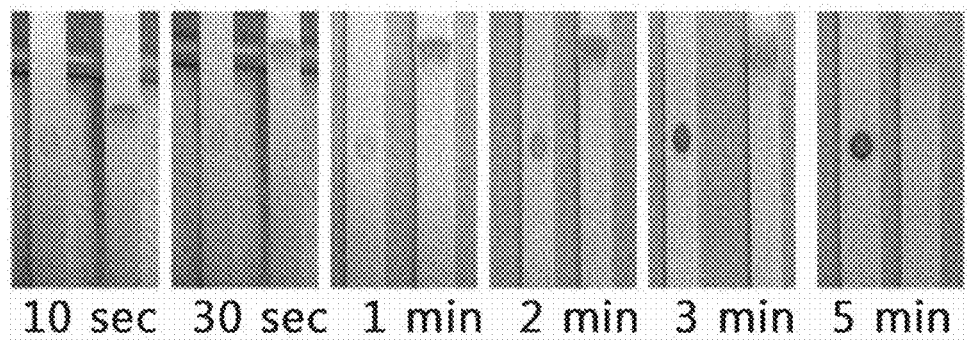
[Fig. 6b]
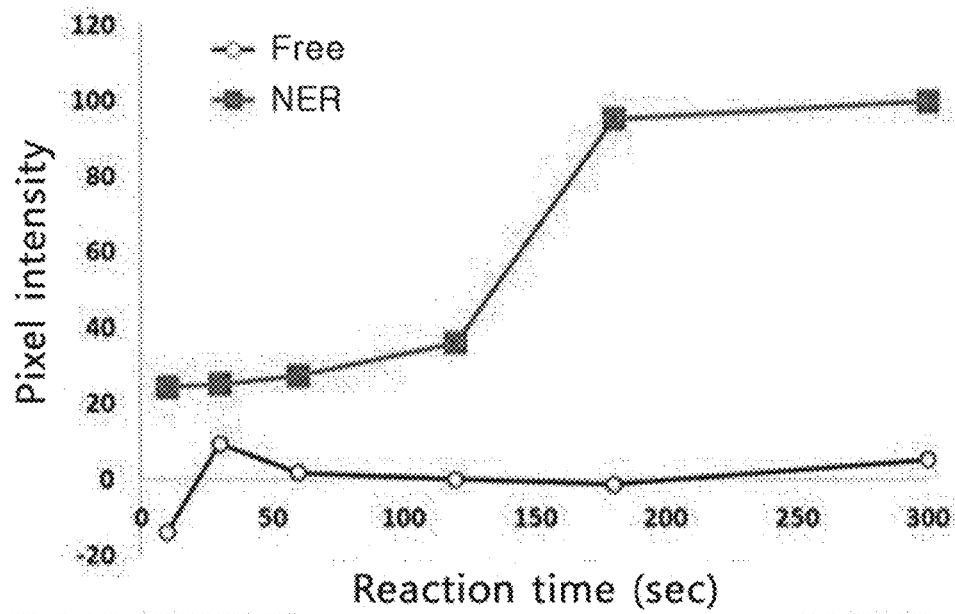

[Fig. 7a]
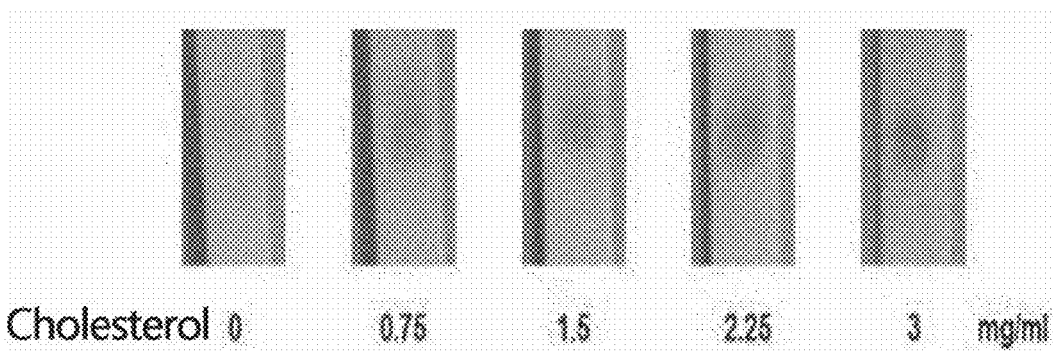
[Fig. 7b]
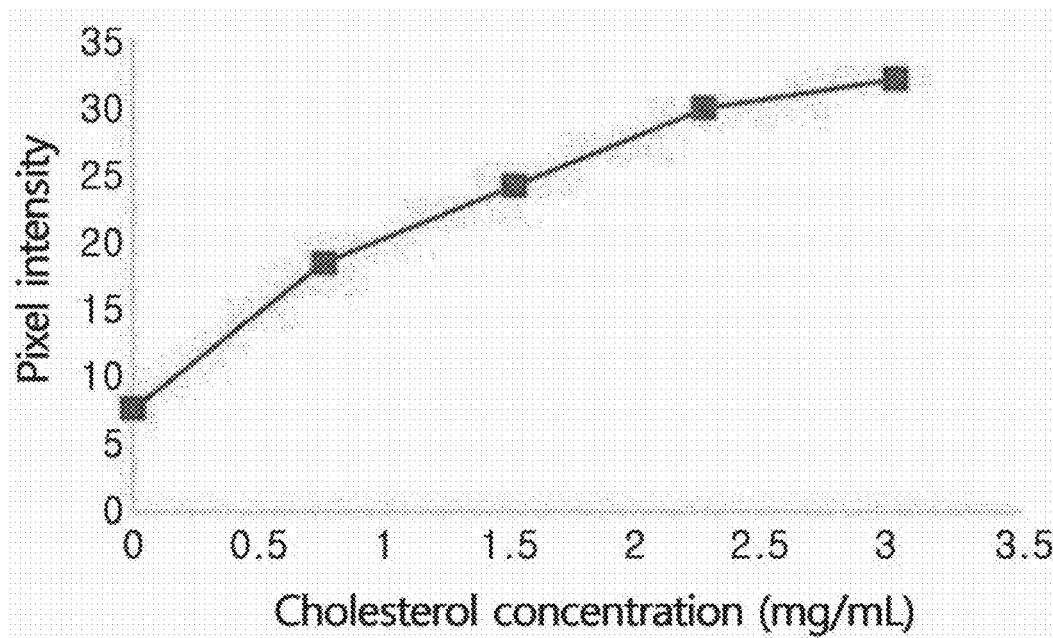

[Fig. 8a]
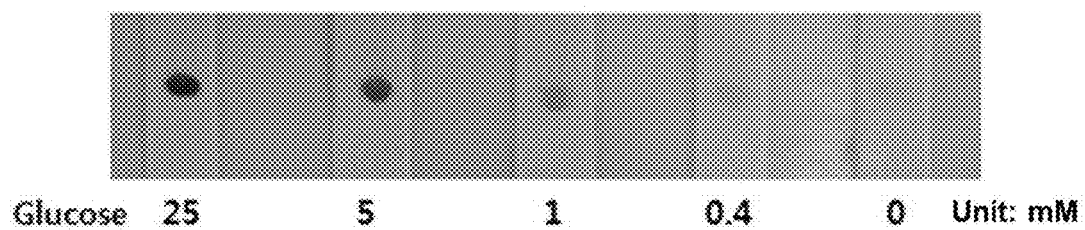

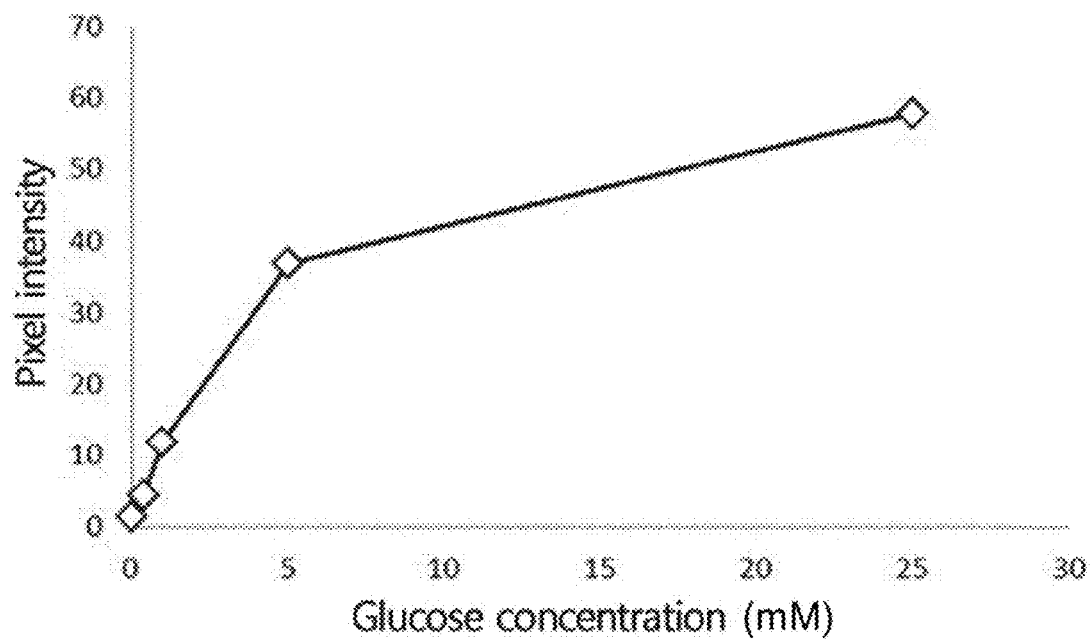

[Fig. 9a]
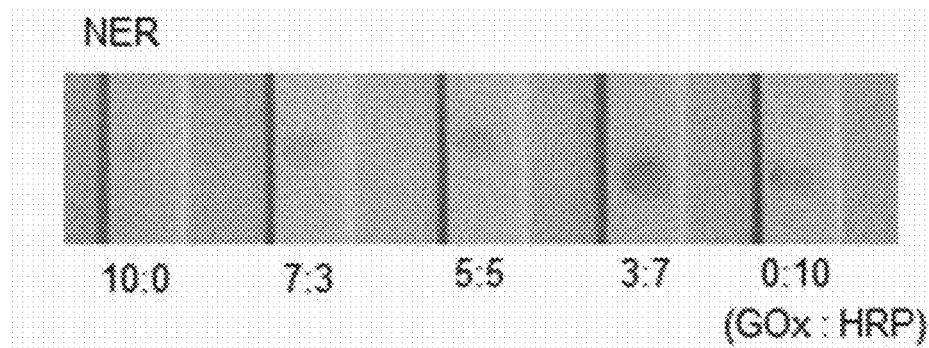
[Fig. 9b]
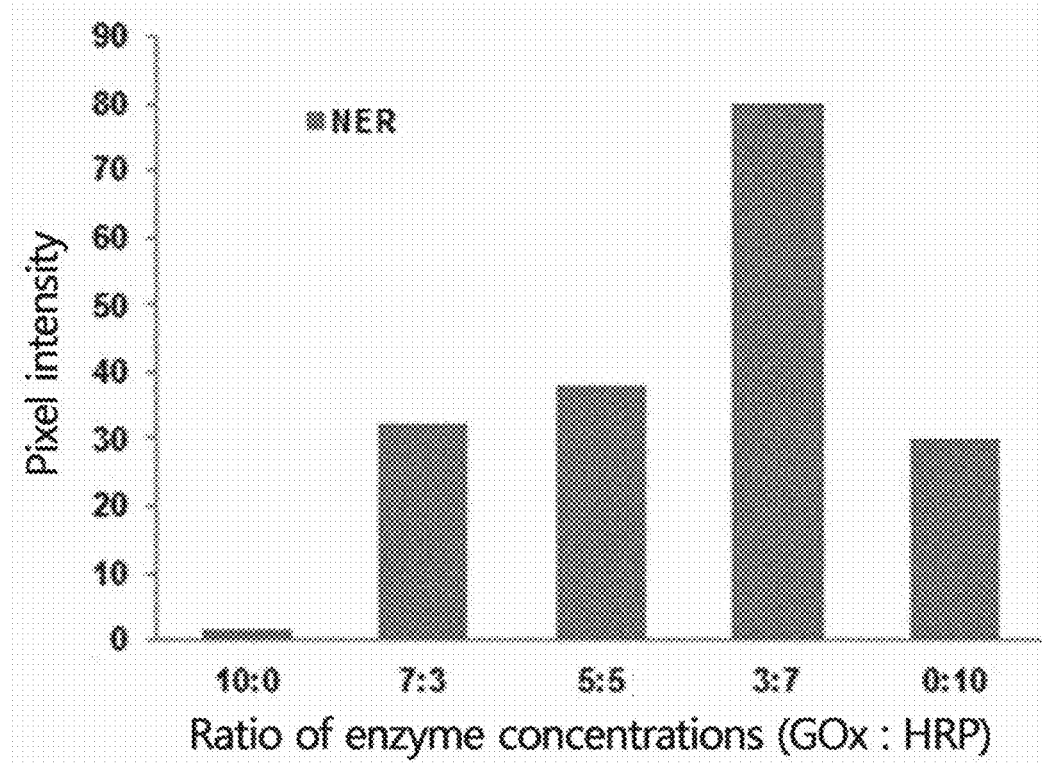

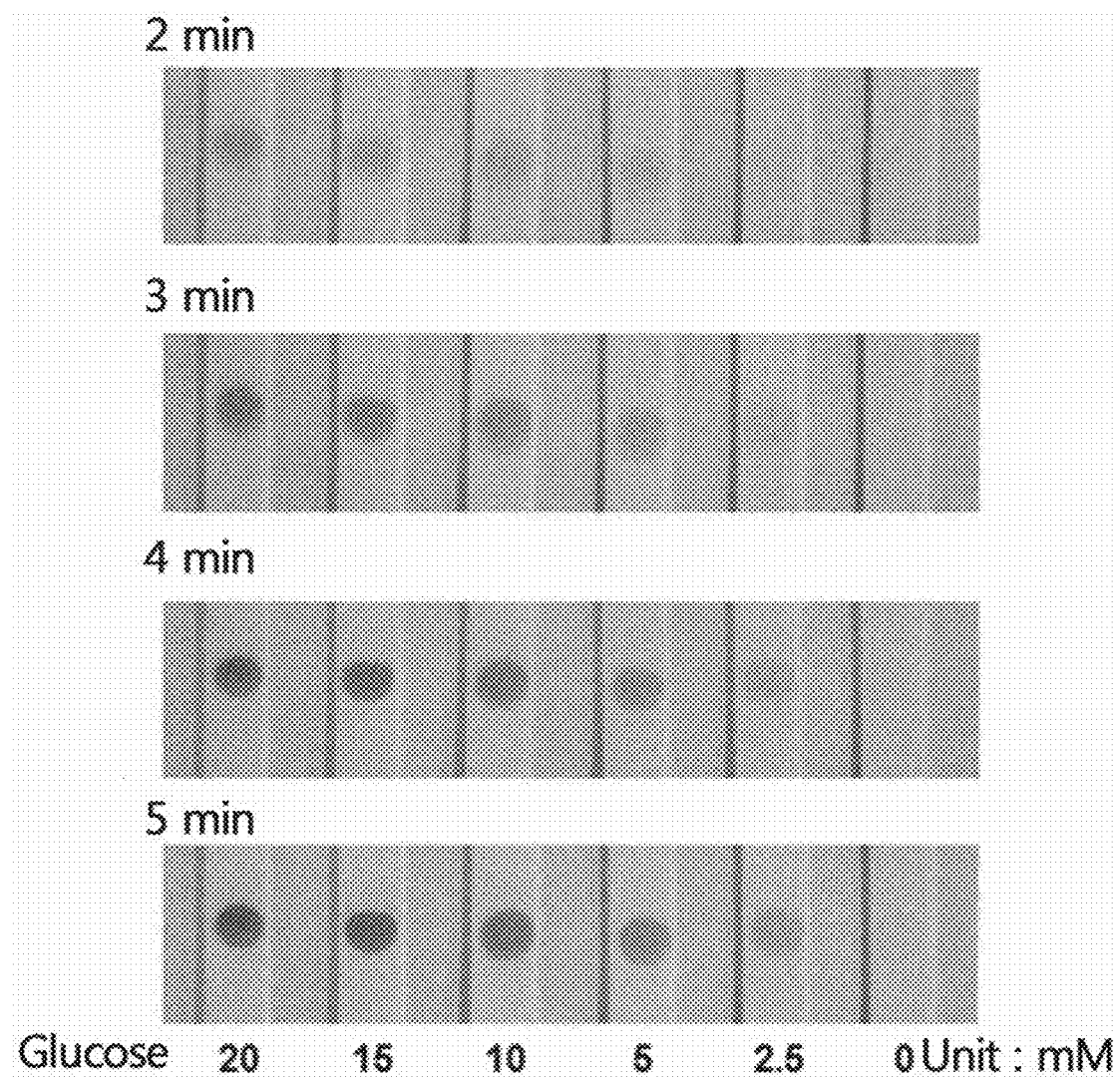

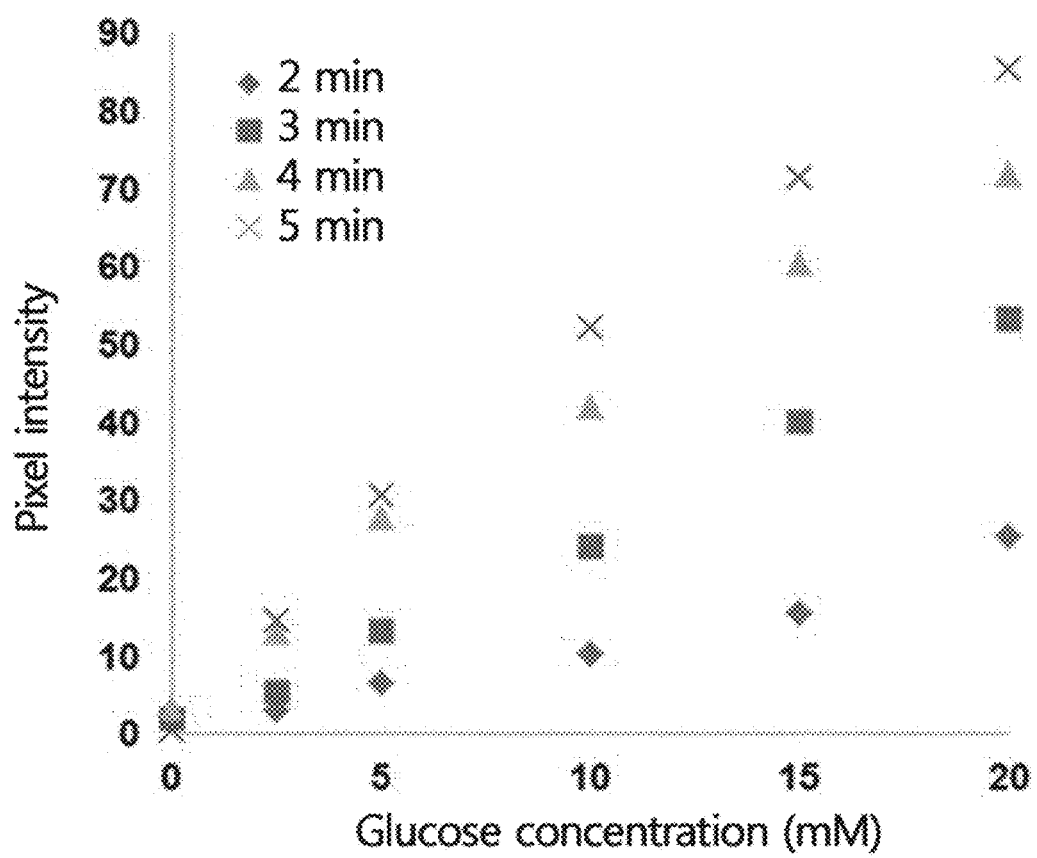
[Fig. 10b]

[Fig. 11]
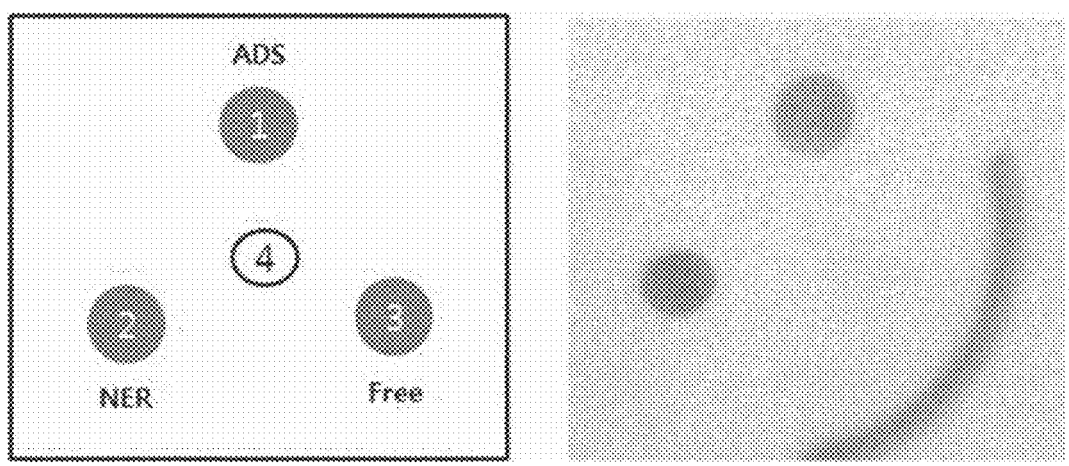

OPTICAL BIOSENSOR

CROSS-REFERENCE TO RELATED APPLICATIONS

This application is a § 371 national stage entry of International Application No. PCT/KR2013/004435, filed May 21, 2013, which claims priority to South Korean Patent Application No. 10-2012-0054343 filed May 22, 2012, the entire contents of which are incorporated herein by reference.

TECHNICAL FIELD

The-present disclosure relates to an optical biosensor, more particularly to an optical biosensor which allows easy quantitative determination and qualitative analysis with remarkably improved sensitivity by concentrating a colorimetric signal from an enzymatic reaction using an enzyme-supported porous support.

BACKGROUND ART

Detection of disease biomarkers (e.g., metabolites, proteins, cells) existing in body fluids (blood, urine, etc.) at low concentrations is usually conducted based on biological reactions such as enzymatic reactions and antigen-antibody interactions. Enzymes and antibodies recognize their targets with very high specificity and also exhibit high reaction efficiency, thus allowing detection of the analyses with high sensitivity. It is important to develop a diagnostic system based on the reaction characteristics to early defect disease-causing biomarkers and to allow for proper treatment in early stages. However, most of the currently available diagnostic systems are limited to laboratory since they require handling of reagents and devices and special techniques for diagnosis.

Recently, as a category in immunoassay, the necessity for early detection of biomarkers that allow estimation of symptoms and progress of human diseases, such as hormones, proteins and microorganisms, is increasing rapidly not only in medical institutions such as hospitals, emergency rooms, etc. but also at home.

For this, an immunoassay system that can be used conveniently in short time without requiring special knowledge or a complicated process is necessary. In general, diagnosis may be accomplished by an immunochromatographic method using a porous membrane as a support for immobilizing a sensing protein (e.g., an antigen or an antibody). If a sample containing an analyte is absorbed into a membrane strip from below, the analyte is transferred by capillary action to the immobilized sensing protein layer through pores. Antigen-antibody interaction occurs on solid surface and unbound components are separated by fluid flow. The membrane strip immunochromatography techniques based on this principle provides a convenient one-step diagnosis in which quick analyte detection is accomplished simply by adding a sample as the transfer of material is accelerated using the lateral flow of fluid.

The demand on the self-diagnostic system is reflected well in the recent rapid market growth of self-diagnostic kits for testing pregnancy and ovulation. In addition, as the establishment of Internet-based remote diagnosis and prescription is expected in the future, a home monitoring system will become a key element for diseases requiring regular diagnosis such as adult diseases.

However, most of the currently available self-diagnostic kits provide only qualitative analysis based on simple immunochromatographic analysis and visual inspection and they are not suitable for the analysis of disease biomarkers (e.g., proteins) that require high-sensitive quantitative analysis such as adult diseases. Although a colorimetric signal generated by a gold conjugate may be converted to optical density for quantitative analysis using an existing optical signal converting means, the detection sensitivity is low as compared to the enzyme immunoassay method widely used in laboratories.

The low sensitivity may be overcome by using high-sensitivity sensing materials such as fluorescent materials or radioisotopes. Indeed, an immunoassay system which performs membrane strip immunochromatographic analysis using a detection antibody labeled with a fluorescent material and interpreting the quantitative result using a fluorescence detector was developed. Recently, this technique has been applied to on-site immunoassay devices that can be used, for example, in emergency rooms because it provides high sensitivity and lacks hazardous elements. However, since the fluorescence detector is relatively too expensive and cannot be made into small size to be porthole, the system is used limitedly in hospitals or clinical laboratories and provides little advantage over the laboratory-scale enzyme immunoassay method except that the analysis time is shorter.

Furthermore, the enzyme immunoassay conducted in laboratories necessarily requires washing in each step of immune reactions to separate the immunoconjugate from unreacted materials and an enzymatic reaction has to be conducted separately for generation of signals. Accordingly, such a complicated multi-step process is not suitable for on-site diagnosis.

Therefore, an optical biosensor capable of easily analyzing a sample with high sensitivity without requiring expensive equipment or reagents is keenly needed.

DISCLOSURE

Technical Problem

The present disclosure is directed to providing an optical biosensor which allows easy quantitative determination and qualitative analysis with remarkably improved sensitivity.

Technical Solution

Hereinafter, the present disclosure is described in more detail referring to the attached drawings.

In a general aspect, the present disclosure provides an optical biosensor including a complex including a porous support and ah enzyme supported inside the pores of the porous support and a method for preparing the same.

As an exemplary embodiment of the present disclosure, the optical biosensor according to the present disclosure may include a complex of a porous support and an oxidase supported inside the pores of the porous support and a chromogenic enzyme.

As another exemplary embodiment of the present disclosure, the present disclosure provides a method for preparing an optical biosensor including a complex of a porous support and an oxidase supported inside the pores of the porous support and a chromogenic enzyme, including:

(1) adsorbing an oxidase inside the pores of a porous support;

(2) coating the porous support-enzyme complex on a sensor surface;

(3) drying the sensor surface; and (4) coating a chromogenic enzyme on the sensor surface.

As another exemplary embodiment of the present disclosure, the present disclosure provides a method for preparing an optical biosensor including a complex of a porous support and an oxidase supported inside the pores of the porous support and a chromogenic enzyme, including:

(1) adsorbing an oxidase inside the pores of a porous support;

(2) forming a porous support-enzyme complex by forming a crosslinkage between the porous support and the enzyme by adding a crosslinking agent to the enzyme-adsorbed porous support;

(3) coating the porous support-enzyme complex on a sensor surface;

(4) drying the sensor surface; and (5) coating a chromogenic enzyme on the sensor surface.

As another exemplary embodiment of the present disclosure, the present disclosure provides a method for preparing an optical biosensor including a complex of a porous support and an oxidase supported inside the pores of the porous support and a chromogenic enzyme, including:

(1) immobilizing an oxidase inside the pores of a porous support through covalent bonding;

(2) coating the resulting porous support-oxidase complex on a sensor surface;

(3) drying the sensor surface; and (4) coating a chromogenic enzyme on the sensor surface.

As another exemplary embodiment of the present disclosure, the present disclosure provides an optical biosensor including a complex of a porous support and a chromogenic enzyme supported inside the pores of the porous support and an oxidase.

As an exemplary embodiment of the present disclosure, the present disclosure provides a method for preparing an optical biosensor including a complex of a porous support and a chromogenic enzyme supported inside the pores of the porous support and an oxidase, including:

(1) adsorbing a chromogenic enzyme inside the pores of a porous support;

(2) coating the resulting porous support-chromogenic enzyme complex on a sensor surface;

(3) drying the sensor surface; and (4) coating an oxidase on the sensor surface.

As another exemplary embodiment of the present disclosure, the present disclosure provides a method for preparing an optical biosensor including a complex of a porous support and a chromogenic enzyme supported inside the pores of the porous support and an oxidase, including:

(1) adsorbing a chromogenic enzyme inside the pores of a porous support;

(2) forming a porous support-chromogenic enzyme complex by forming a crosslinkage between the porous support and the chromogenic enzyme by adding a crosslinking agent to the enzyme-adsorbed porous support;

(3) coating the porous support-chromogenic enzyme complex on a sensor surface;

(4) drying the sensor-surface; and (5) coating an oxidase on the sensor surface.

As another exemplary embodiment of the present disclosure, the present disclosure provides a method for preparing an optical biosensor including a complex of a porous support and a chromogenic enzyme supported inside the pores of the porous support and an oxidase, including:

(1) immobilizing a chromogenic enzyme inside the pores of a porous support through covalent bonding;

(2) coating the resulting porous support-chromogenic enzyme complex on a sensor surface;

(3) drying the sensor surface; and (4) coating an oxidase oh the sensor surface.

As another exemplary embodiment of the present disclosure, the present disclosure provides an optical biosensor including a complex of a porous support and an oxidase and a chromogenic enzyme supported inside the pores of the porous support.

As an exemplary embodiment of the present disclosure, the present disclosure provides a method for preparing an optical biosensor including a complex of a porous support and an oxidase and a chromogenic enzyme supported inside the pores of the porous support, including:

(1) adsorbing an oxidase and a chromogenic enzyme inside the pores of a porous support; and (2) coating the resulting porous support-oxidase-chromogenic enzyme complex on a sensor surface.

As another exemplary embodiment of the present disclosure, the present disclosure provides a method for preparing an optical biosensor including a complex of a porous support and an oxidase and a chromogenic enzyme supported inside the pores of the porous support, including:

(1) adsorbing an oxidase and a chromogenic enzyme inside the pores of a porous support;

(2) forming a porous support-oxidase-chromogenic enzyme complex by forming a crosslinkage between the porous support and the enzymes by adding a crosslinking agent to the enzyme-adsorbed porous support; and (3) coating the porous support-oxidase-chromogenic enzyme complex on a sensor surface.

As another exemplary embodiment of the present disclosure, the present disclosure provides a method for preparing an optical biosensor including a complex of a porous support and an oxidase and a chromogenic enzyme supported inside the pores of the porous support, including:

(1) immobilizing an oxidase and a chromogenic enzyme inside the pores of a porous support through covalent bonding; and (2) coating the resulting porous support-oxidase-chromogenic enzyme complex on a sensor surface.

The oxidase may be one or more selected from a group consisting of glucose oxidase, cholesterol oxidase, polyphenol oxidase, monoamine oxidase, xanthine oxidase, cytochrome oxidase, ascorbic acid oxidase and D-arabino-1,4-lactone oxidase.

The chromogenic enzyme may be one or more selected from a group consisting of peroxidase, alkaline phosphatase, tyrosinase, laccase, acetylcholinesterase and β-galactosidase.

The porous support may be one or more selected from a group consisting of silica, alumina, niobium, tantalum, zirconium, titanium and a vinyl polymer.

The crosslinking agent may be one or more selected from a group consisting of glutaric dialdehyde, diisocyanate, dianhydride, diepoxide, dialdehyde, diimide, 1-ethyl-3-dimethyl aminopropylcarbodiimide, bisimidoester, bis(succinimidyl ester) and diacid chloride.

In the complex of the oxidase and the chromogenic enzyme supported on the support, a ratio of the oxidase to the chromogenic enzyme may be from 1:9 to 9:1. Specifically, when the oxidase is glucose oxidase is and the chromogenic enzyme is horseradish peroxidase, a ratio of the glucose oxidase to the horseradish peroxidase may be from 2:8 to 4:6.

Advantageous Effects

Since a dye does not flow but is concentrated in one place by a porous enzyme sopped, an optical biosensor of the present disclosure has remarkably improved sensitivity. In addition, since a predetermined amount of sample that can be held by the enzyme support participates in a reaction, measurement reproducibility is improved and analysis is possible with a small quantity of sample. It is possible to carry out quantitative determination and qualitative analysis since color intensity increases with time. Also, since various chromogenic substrates can be used depending on analytes or environments, the sensor can be used for various applications.

BRIEF DESCRIPTION OF DRAWINGS

FIG. 1 schematically shows a strip sensor according to an exemplary embodiment of the present disclosure.

FIG. 2 shows a TEM image of porous silica that can be used in the present disclosure.

FIG. 3a shows photographs obtained after coating porous silica on which two enzymes for blood glucose measurement (glucose oxidase (GOx) and horseradish peroxidase (HRP)) are immobilized at various ratios (GOx:HRP=10:0, 7:3, 5:5, 3:7, 0:10) on a membrane and flowing a sample containing glucose and a dye for 3 minutes, and FIG. 3b shows pixel intensity at the coated portion.

FIG. 4 schematically describes synthesis of an enzyme-porous support complex by simple adsorption, covalent bonding and crosslinkage between enzymes using the nanoscale enzyme reactor method.

FIG. 5 shows the stability of free cholesterol oxidase (COx), cholesterol oxidase simple adsorbed on porous silica (adsorbed cholesterol oxidase, ADS-COx), and cholesterol oxidase immobilized on porous silica using the nanoscale enzyme reactor method (nanoscale enzyme reactor cholesterol oxidase, NER-COx) with time under the condition of stirring with 200 rpm at 40° C.

FIG. 6a shows photographs showing color development at a portion where free enzyme (right) or enzyme-immobilized porous silica (left) is coated with time while a sample flows through a membrane, and FIG. 6b shows pixel intensity at the coated portion.

FIG. 7a shows a result of measuring cholesterol concentration using enzyme-supported porous silica, and FIG. 7b shows pixel intensity.

FIG. 8a shows a photograph obtained after coating chromogenic enzyme-immobilized porous silica, adding glucose oxidase and flowing a sample containing glucose and a dye for 3 minutes, and FIG. 8b shows pixel intensity at the coated portion.

FIG. 9a shows photographs obtained after coating porous silica on which two enzymes for blood glucose measurement (glucose oxidase (GOx) and horseradish peroxidase (HRP)) are immobilized at various ratios (GOx:HRP=10:0, 7:3, 5:5, 3:7, 0:10) using the nanoscale enzyme reactor method on a membrane and flowing a sample containing glucose and a dye for 3 minutes, and FIG. 9b shows pixel intensity at the coated portion.

FIG. 10a shows photographs obtained at different times using porous silica on which GOx and HRP are immobilized at a ratio of 3:7 using the nanoscale enzyme reactor method after flowing glucose at various concentrations, and FIG. 10b shows pixel intensity at the coated portion.

FIG. 11 schematically shows positions of porous silica on which GOx and HRP are immobilized at a ratio of 3:7 by simple adsorption (ADS) or using the nanoscale enzyme reactor (NER) method and free GOx and HRP on a sensor surface (left) and a photograph obtained after flowing 10 mM glucose at the center for 3 minutes.

BEST MODE

FIG. 1 schematically shows a strip sensor according to an exemplary embodiment of the present disclosure. Specifically, a sample (blood) is injected to a sample pad and the sample is transferred to a substrate pad by capillary action. The substrate pad contains N,N-bis(4-sulfobutyl)-3,5-dimethylaniline disodium salt (MADB) and 4-aminoantipyrine (AAP) for color development by a dye. The MADB and AAP contained in the substrate pad are transferred to an analysis pad along with the sample.

In an exemplary embodiment of the present disclosure, cholesterol oxidase may be used as an enzyme.

In this case, in the analysis pad, cholesterol oxidase is supported inside the pores of a porous support (porous silica). When the sample is introduced into the pores of the porous support, a reaction as described in Scheme 1 occurs. Scheme 3 describes formation of a dye by oxidative coupling between MADB and AAP as part of Scheme 2.

[Scheme 1]

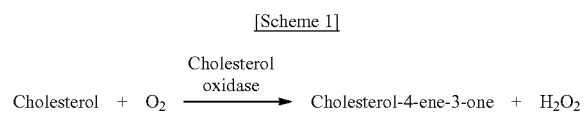

Cholesterol + $O_2$ $\xrightarrow{\text{Cholesterol oxidase}}$ Cholesterol-4-ene-3-one + $H_2O_2$

[Scheme 2]

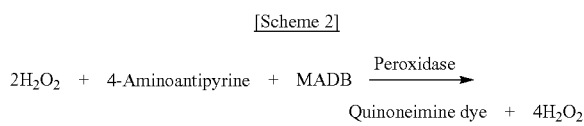

$2H_2O_2$ + 4-Aminoantipyrine + MADB $\xrightarrow{\text{Peroxidase}}$ Quinoneimine dye + $4H_2O_2$

[Scheme 3]

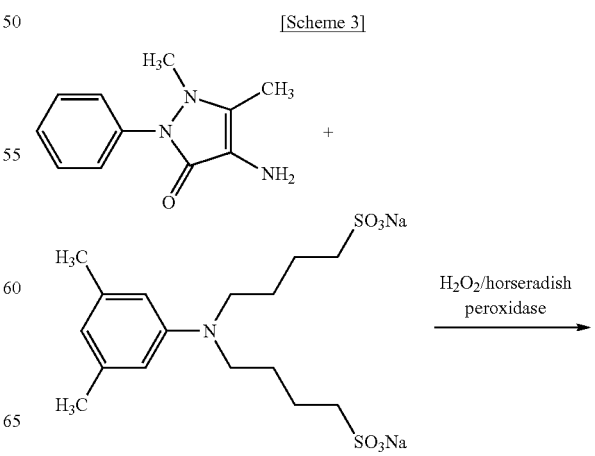

-continued

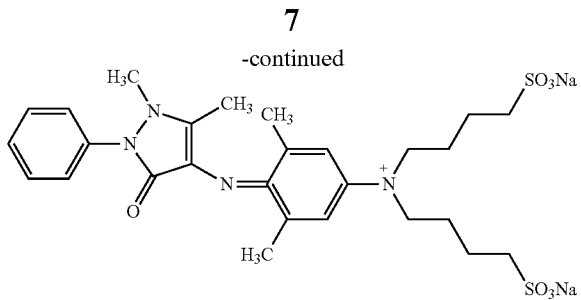

Specifically, hydrogen peroxide is produced from cholesterol contained in the sample by the cholesterol oxidase immobilized inside the porous support (Scheme 1). The hydrogen peroxide is used to produce a dye (quinoneimine dye) through oxidative coupling of MADB and AAP by HRP as described in Schemes 2 and 3. The dye exhibits blue color that can be measured at 630 nm. By monitoring color change, the amount of the sample can be measured quantitatively.

In another exemplary embodiment of the present disclosure, glucose oxidase may be used as the enzyme. In this case, in the analysis pad, glucose oxidase is supported inside the pores of the porous support (porous silica). When the sample is introduced into the pores of the porous support, a reaction as described in Scheme 4 occurs. The subsequent reaction is the same as that for cholesterol oxidase described in Schemes 2 and 3. That is to say, hydrogen peroxide is produced from glucose contained in the sample by the glucose oxidase immobilized inside the porous support (Scheme 4). The hydrogen peroxide is used to produce a dye (quinoneimine dye) through oxidative coupling of MADB and AAP by HRP as described in Schemes 2 and 3.

[Scheme 4]

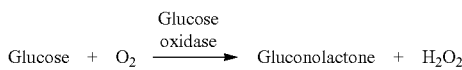

By controlling the structure and physical properties of the porous support such that the dye cannot easily escape out of the porous support, most of the dye produced according to Schemes 1 and 2 remains inside the pores of the support. If the dye escapes out of the porous support, the dye is dispersed broadly, thereby resulting in decreased optical signals and decreased measurement reproducibility. Since the dye remains on the sensor surface without escaping out of the sensor surface, very strong color intensity can be achieved and maximum light emission is possible with a minimal small amount of sample. Also, in addition to the oxidase such as cholesterol oxidase, HRP or a chromogenic precursor may also be present inside the porous support.

The porous support that can be used in the present disclosure is not particularly limited as long as it is one that can immobilize an enzyme, a chromogenic precursor, an antibody, a metal particle, a gene, a compound, etc., allows flowing of an enzyme, a sample, a chromogenic precursor, etc. thereinto, allows a dye produced from an enzymatic reaction to remain effectively and is transparent such that color change can be observed from outside.

Specifically, the porous support may be made from one or more material selected from silica, alumina, niobium, tantalum, zirconium, titanium and a divinylbenzene polymer.

The porous support of the present disclosure may also contain a functional group that can form covalent bonding with an enzyme, a chromogenic precursor, etc. inside the pores. For this, a pretreatment process of forming a functional group inside the pores of the porous support or on the surface of the support may be conducted before supporting the enzyme. The functional group is not particularly limited as long as it can form covalent bonding with an enzyme as being formed inside the pores or on the support surface. Specifically, it may be an amino group, a carboxyl group, an aldehyde group, an epoxy group, a hydroxyl group, a thio group, etc.

Through covalent bonding with the functional group, an enzyme may be supported or bound inside the pores or on the support surface.

In an exemplary embodiment of the present disclosure, the enzyme may be simply adsorbed inside the pores of the support. Alternatively, if a functional group capable of forming covalent bonding with the enzyme exists inside the pores, the enzyme may be covalently bonded inside the pores.

In another exemplary embodiment of the present disclosure, the enzyme may be simply adsorbed and then cross-linked to form a crosslinked enzyme aggregate. Specifically, when a crosslinking agent is added to the enzymes contained inside the pores (being adsorbed or covalently bonded to the walls of the pores), a crosslinked enzyme aggregate is formed as crosslinkage is formed between the enzymes adsorbed inside the pores. The resulting crosslinked enzyme aggregate becomes larger in size than the opening of the pores and, as a result, a remarkably large amount of enzymes can be supported inside the support. In addition, since the enzyme aggregate remains without leaving the pores, the enzyme aggregate can be contained inside the porous support for a long period of time even when no direct bonding such as covalent bonding is formed between the porous support and the enzyme.

Furthermore, if the pores of the porous support are curved, the crosslinked enzyme aggregate may be prevented from escaping. In addition, if the inside of the pores is modified, covalent bonding may be formed between the crosslinked enzyme and the support.

In another exemplary embodiment of the present disclosure, a dye may be supported and bound inside the pores of the porous support and an enzyme may be flown into the pores of the support later.

In an exemplary embodiment of the present disclosure, the optical biosensor according to the present disclosure may be a strip type sensor and it is not limited in material as long as a sample can be flown by capillary action. Specifically, the optical biosensor may be made from nitrocellulose, although not being limited thereto. In particular, a porous membrane may be used for a strip type sensor. A symmetric membrane or an asymmetric membrane may be used. Since the membrane has micropores, a sample can be transferred to the opposite end of the membrane through capillary action. The rate of sample transfer depends on the size of the micropores. The rate is lower if the pores size is larger whereas the rate is higher if the pores size is smaller. The symmetric membrane refers to one having micropores of the same size and the asymmetric membrane refers to one having micropores of different sizes. The pore size of the asymmetric membrane increases toward the opposite end.

The optical biosensor of the present disclosure may be used as an optical biosensor for measuring colorimetric signals. The biosensor may exhibit high detection sensitivity as an enzymatic reaction is conducted independently on a membrane strip as in the enzyme-linked immunosorbent assay (ELISA) using a microwell plate for immobilizing proteins and may be used for quick measurement like in the general immunochromatography assay. The sensor for measuring colorimetric signals may measure the intensity of colorimetric signals generated on a membrane proportionally to the analyte concentration in the sample by reflectance photometry. Accordingly, since a small-sized equipment can be used for detecting signals when compared with the fluorescence measurement system which is used for relatively sensitive quantitative measurement, the sensor is applicable to on-site diagnosis.

The enzyme used to generate colorimetric signals may be peroxidase, alkaline phosphatase (AP), tyrosinase, laccase, acetylcholinesterase, β-galactosidase, etc. which are generally used in enzyme immunoassay. These enzymes exhibits color as a result of catalytic reactions and different substrates are used for each enzyme. For example, when peroxidase is used, tetramethylbenzidine (TMB), diaminobenzidine (DAB), 2,2'-azino-bis(3-ethylbenzothiazoline-6-sulphonic add (ABTS), 4-chloro-1-naphthol (4C1N), etc. which may be deposited on a membrane in the presence of hydrogen peroxide may be used as a chromogenic substrate. And, when AP is used, BCIP (5-bromo-4-chloro-3-indolyl phosphate p-toluidine salt)/NBT (nitro-blue tetrazolium chloride), etc. may be used. Since each substrate has different optimal reaction condition, an adequate substrate may be selected considering the analysis characteristics of the biosensor and other requirements.

After the enzyme, gene, antibody, metal, compound, etc. used for the analysis of a sample is supported inside the porous support, a reaction for generating signals such as a color reaction may occur as a sample passes through the porous support.

The enzyme may be labeled by directly polymerizing the enzyme with a detection antibody as described above or indirectly using a secondary antibody-enzyme conjugate specific for the detection antibody.

As another method of generating signals, the binding between streptavidin and biotin may be used. Typically, streptavidin is polymerized with a detection antibody and biotin is polymerized with an enzyme. Since the binding between streptavidin and biotin has higher affinity as compared to the general antigen-antibody bindings, signals can be enhanced more effectively as compared to the method using a secondary antibody. The method for generating signals may be selected considering the detection limit of the analyte, range of detection concentration, analysis time, economy, and so forth.

When preparing a biosensor for measuring colorimetric signals, chemical reactions such as a catalytic reaction between gold and silver may be employed instead of the enzymatic catalytic reaction. Typically, colloidal gold and silver acetate may be used. Introduction of colloidal gold and silver acetate info the porous support provides the advantage that analysis of a low-concentration analyte is possible. The generated colorimetric signals may be detected by reflectance photometry as in the enzyme-based method.

Mode for Invention

Hereinafter, the present disclosure will be described in detail through examples. However, the following examples are for illustrative purposes only and it will be apparent to those of ordinary skill in the art that the scope of the present disclosure is not limited by the examples.

EXAMPLE 1

Preparation of Complex of Oxidase and Chromogenic Enzyme Supported Inside Pores of Porous Support A complex of an oxidase and a chromogenic enzyme supported inside the pores of a porous support was prepared. Specifically, glucose oxidase (GOx) and horseradish peroxidase (HRP) were dissolved in a 100 mM phosphate buffer (pH 7.0) at various ratios (GOx:HRP=10:0, 7:3, 5:5, 3:7, 0:10) and 2 ml (10 mg/mL) was added to 5 mg of porous silica particles as shown in FIG. 2 and stirred at 200 rpm for 1 hour. After removing unadsorbed enzymes through centrifugation, the remainder was washed with a phosphate buffer. Then, the complex-containing solution was stirred with a 100 mM Tris buffer (pH 7.6) at 200 rpm for 30 minutes and washed again with a phosphate buffer. The resulting enzyme-immobilized substance was kept at 4° C. to prepare a complex of an oxidase and a chromogenic enzyme supported inside the pores of a porous support.

EXAMPLE 2

Measurement of Blood Glucose Level Using Complex of Oxidase and Chromogenic Enzyme Supported Inside Pores of Porous Support 2 μL (50 mg/mL) of the simple adsorption (ADS) of an oxidase and a chromogenic enzyme prepared in Example 1 was coated on a membrane and then dried. After flowing a 10 mM glucose solution containing 50 mM AAP and MADB, a reaction was conducted for 1 minute. FIG. 3a compares the color reactions of the samples 1 minute later. The sample wherein glucose oxidase and horseradish peroxidase were immobilized at a ratio of 3:7 using the simple adsorption (ADS) method showed the most intense color reaction. In contrast, no signal could be detected for the sample wherein free glucose oxidase and horseradish peroxidase were used (right). FIG. 3b shows the pixel intensity using image software at the portion where the enzyme-immobilized silica particles are coated (dotted line). It can be seen that the sample wherein GOx and HRP are immobilized at a ratio of 3:7 exhibits remarkably high intensity.

EXAMPLE 3

Preparation of Enzyme-Porous Silica Particle Complex Using Nanoscale Enzyme Reactor (NER) Method An enzyme-porous silica particle complex was prepared by forming crosslinkage between enzyme particles using the nanoscale enzyme reactor (NER) method according to the present disclosure as shown in FIG. 4. Specifically, cholesterol oxidase was dissolved in a 100 mM phosphate buffer (pH 7.0) and 2 ml (10 mg/mL) was added to 5 mg of porous silica particles as shown in FIG. 2 and stirred at 200 rpm for 1 hour. After removing unadsorbed enzymes through centrifugation, 1 ml of a 0.1 v/v % glufaric dialdehyde solution was added. Then, after stirring at 200 rpm at room temperature for 1 hour to allow sufficient crosslinking by the crosslinking agent, the solution was washed again with a phosphate buffer. Then, the complex-containing solution was stirred with a 100 mM Tris buffer (pH 7.6) at 200 rpm for 30 minutes and washed again with a phosphate buffer. The resulting enzyme-immobilized substance was kept at 4° C. to prepare a nanoscale enzyme reactor (NER) as an enzyme-porous silica particle complex.

EXAMPLE 4

Measurement of Stability of Enzyme-Supported Porous Silica

The activity of the nanoscale enzyme reactor prepared in Example 3 was measured based on oxidation of cholesterol dissolved using a surfactant (Triton X-100). FIG. 5 shows the stability of free COx, ADS-COx and NER-Cox under stirring at 200 rpm at 40° C. Each sample was kept under stirring at 200 rpm at 40° C. and part of each sample was taken for activity measurement. The activity of free Cox decreased to less than 50% of the initial activity in 4 hours and that of ADS also decreased to below 50% of the initial activity in 5 hours. In contrast, the activity of NER-Cox was maintained at 70% of the initial activity even 60 hours later Accordingly, it can be seen that the enzyme-supported porous silica of the present disclosure has remarkably improved stability.

EXAMPLE 5

Detection of Cholesterol Using Enzyme-Porous Silica Particle Complex at Different Times 1.5 mg/mL cholesterol was detected at different times using the strip sensor shown in FIG. 1 (see FIG. 8). For NER-Cox (left), 4 μL of 50 mg/mL porous silica was coated. For free enzyme (right), 1 μL of 7 U/ml cholesterol oxidase was coated and dried. After coating 20 mM N,N-bis(4-sulfobutyl)-3,5-dimethylaniline disodium salt (MADB), 20 mM 4-aminoantipyrine (AAP) and 20 U/ml horseradish peroxidase (HRP) dissolved in a 50 mM 3-(4-morpholino) propanesulfonic acid (MOPS) buffer (pH 5.0) on a substrate pad and drying at 60° C. for 15 minutes, 100 μL of cholesterol dissolved in 5% 1-methyl-2-pyrrolidone as an organic solvent and 2% Thesit as a surfactant was loaded onto a sample pad. Then, the change of the membrane was monitored by taking pictures at predetermined times and the pixel intensity of the enzyme-coated portion was quantitated. Although MADB exhibits relatively superior stability in dry state when compared with other chromogenic substrates, it cannot provide correct colorimetric signals because it is highly soluble and flows along with a solution when used for an optical strip sensor. However, if the enzyme-immobilized porous silica is used, signals can be accumulated even when a water-soluble chromogenic substrate is used and, accordingly, the sensitivity of an optical sensor can be enhanced and the stability of the strip itself can be improved. As can be seen from FIG. 7a, the colorimetric signals from MADB were accumulated and thus the cholesterol concentration could be determined therefrom. As a result, the calibration curve of FIG. 7b was obtained.

EXAMPLE 6

Measurement of Blood Glucose Level Using Enzyme-Porous Silica Particle Complex

Blood glucose level was measured using the strip sensor of FIG. 1 based on the change in pixel intensity depending on glucose concentration (see FIG. 8). 4 μL of 50 mg/mL NER-HRP porous silica was coated and 1 μL of 2 KU/mL glucose oxidase was coated and dried for blood glucose level measurement 20 mM MADB and AAP were coated on a substrate pad. Glucose was dissolved in a PBS buffer (pH 7.0) at different concentrations and 100 μL was loaded on a sample pad. 3 minutes later, the change in the membrane was observed by faking photographs and the pixel intensify at the enzyme-coated portion was quantitated. As a result, the calibration curve of FIG. 8b was obtained.

EXAMPLE 7

Preparation of Enzyme-Co-Immobilized Porous Silica Particle Complex Using Nanoscale Enzyme Reactor (NER) Method An enzyme-porous silica particle complex wherein two enzymes are co-immobilized for blood glucose level measurement was prepared according to the present disclosure as shown in FIG. 4. Specifically, glucose oxidase (GOx) and horseradish peroxidase (HRP) were dissolved in a 100 mM phosphate buffer (pH 7.0) at various ratios (GOx:HRP=10:0, 7:3, 5:5, 3:7, 0:10) and 2 ml (10 mg/mL) was added to 5 mg of porous silica particles as shown in FIG. 2 and stirred at 200 rpm for 1 hour. After removing unadsorbed enzymes through centrifugation, 1 ml of a 0.1 v/v % glutaric dialdehyde solution was added. Then, after stirring at 200 rpm at room temperature for 1 hour to allow sufficient crosslinking by the crosslinking agent, the solution was washed again with a phosphate buffer. Then, the complex-containing solution was stirred with a 100 mM Tris buffer (pH 7.6) at 200 rpm for 30 minutes and washed again with a phosphate buffer. The resulting enzyme-immobilized substance was kept at 4° C. to prepare a nanoscale enzyme reactor (NER-GOx&HRP) as an enzyme-co-immobilized porous silica particle complex.

EXAMPLE 8

Measurement of Blood Glucose Level Using Enzyme-Co-Immobilized Porous Silica Particle Complex Prepared Using Nanoscale Enzyme Reactor (NER) Method 2 μL (50 mg/mL) of the enzyme-co-immobilized porous silica particle complex prepared in Example 7 was coated on a membrane and then dried. After flowing a 10 mM glucose solution containing 50 mM AAP and MADB, a reaction was conducted for 1 minute. FIG. 9a compares the color reactions of the samples 1 minute later. The sample wherein glucose oxidase and horseradish peroxidase were immobilized at a ratio of 3:7 using the nanoscale enzyme reactor method showed the most intense color reaction. FIG. 9b shows the pixel intensity at the portion where the enzyme-immobilized silica particles are coated. It can be seen that the sample wherein GOx and HRP are immobilized at a ratio of 3:7 exhibits remarkably high intensity.

FIG. 10a shows photographs obtained at different times using the nanoscale enzyme reactor on which GOx and HRP are immobilized at a ratio of 3:7 after flowing glucose at various concentrations, and FIG. 10b shows pixel intensity at the coated portion.

EXAMPLE 9

Measurement of Blood Glucose Level Using Enzyme Co-Immobilization-Porous Silica Particle Complex on Broad Sensor Surface 10 μL (50 mg/mL) of each of the enzyme-co-immobilized porous silica particle complex prepared by simple adsorption and using the nanoscale enzyme reactor method in Example 1 and Example 7 or 10 μL of a mixture of free GOx and HRP (GOx:1 U/ml, HRP:1 U/mL) was applied on a membrane sensor surface and then dried. After flowing 10 mM glucose containing 50 mM AAP and MADB, a reaction was conducted for 3 minutes. As for the free enzymes, few signals were detected as the dye diffused along the flow of the solution. In contrast, strong signals were detected for the ADS or NER samples as the dye was deposited.

INDUSTRIAL APPLICABILITY

Since various chromogenic substrates can be used depending on analytes or environments, the sensor according to the present disclosure can be used for various applications.

The invention claimed is:

1. A strip type optical biosensor comprising a complex of a porous support and at least one of:
   (1) an oxidase supported inside the pores of the porous support and a chromogenic enzyme;
   (2) a chromogenic enzyme supported inside the pores of the porous support and an oxidase; and
   (3) an oxidase and a chromogenic enzyme supported inside the pores of the porous support,
   wherein the porous support is on a porous sensor strip membrane at a medial portion of the porous sensor strip membrane, said porous sensor strip membrane being of elongate form and adapted to receive a sample at an end portion of the porous sensor strip membrane for flow of the sample through the porous sensor strip membrane from said end portion thereof to the porous support at the medial portion of the porous sensor strip membrane, wherein a chromogenic material is generated in the pores of the porous support by a catalytic reaction of the oxidase and the chromogenic enzyme with a target analyte to produce a colorimetric signal from the chromogenic material in the porous support, wherein the porous support retains the chromogenic material for optical analysis of said colorimetric signal, and wherein the porous sensor strip membrane is adapted for said flow of a sample therethrough from said end portion of the porous sensor strip membrane to the porous support at the medial portion of the porous sensor strip membrane for enzyme-catalyzed reaction in the pores of the porous support to produce said colorimetric signal when the target analyte is present in said sample.

2. The strip type optical biosensor according to claim 1, wherein the oxidase is one or more selected from a group consisting of glucose oxidase, cholesterol oxidase, polyphenol oxidase, monoamine oxidase, xanthine oxidase, cytochrome oxidase, ascorbic acid oxidase and D-arabino-1,4-lactone oxidase.

3. The strip type optical biosensor according to claim 1, wherein the chromogenic enzyme is one or more selected from a group consisting of peroxidase, alkaline phosphatase, tyrosinase, laccase, acetylcholinesterase and β-galactosidase.

4. The strip type optical biosensor according to claim 1, wherein the porous support is one or more selected from a group consisting of silica, alumina, niobium, tantalum, zirconium, titanium and a vinyl polymer.

5. The strip type optical biosensor of claim 1, comprising multiple porous supports on the porous sensor strip membrane, each having at least one of the oxidase and the chromogenic enzyme supported inside the pores thereof for said enzyme-catalyzed reaction in the pores of the porous support to produce said colorimetric signal when the target analyte is present in said sample.

6. A method for preparing a strip type optical biosensor as claimed in claim 1, comprising a complex of a porous support and an oxidase supported inside the pores of the porous support and a chromogenic enzyme, said method comprising:
   (1) at least one of:
      (a) adsorbing the oxidase inside the pores of the porous support to form a porous support-oxidase complex,
      (b) adsorbing the oxidase inside the pores of the porous support to form an oxidase-adsorbed porous support, and forming a porous support-oxidase complex by forming a crosslinkage between the oxidase molecules by adding a crosslinking agent to the oxidase-adsorbed porous support, and
      (c) immobilizing the oxidase inside the pores of the porous support through covalent bonding to form a porous support-oxidase complex;
   (2) coating the porous support-oxidase complex on a medial portion of a porous sensor strip membrane;
   (3) drying the porous sensor strip membrane; and
   (4) coating the chromogenic enzyme on the porous sensor strip membrane, arranged so that the oxidase of the porous support-oxidase complex and the chromogenic enzyme will catalytically react with a target analyte to generate a chromogenic material in the porous support and produce a colorimetric signal from the chromogenic material in the porous support, and wherein the porous support retains the chromogenic material for optical analysis of said colorimetric signal, so that the chromogenic material remains in the pores of the porous support and is prevented from escaping from the porous support.

7. The method for preparing a strip type optical biosensor according to claim 6, wherein the oxidase is one or more selected from a group consisting of glucose oxidase, cholesterol oxidase, polyphenol oxidase, monoamine oxidase, xanthine oxidase, cytochrome oxidase, ascorbic acid oxidase and D-arabino-1,4-lactone oxidase.

8. The method for preparing a strip type optical biosensor according to claim 6, wherein the chromogenic enzyme is one or more selected from a group consisting of peroxidase, alkaline phosphatase, tyrosinase, laccase, acetylcholinesterase and β-galactosidase.

9. The method for preparing a strip type optical biosensor according to claim 6, wherein the crosslinking agent is one or more selected from a group consisting of glutaric dialdehyde, diisocyanate, dianhydride, diepoxide, dialdehyde, diimide, 1-ethyl-3-dimethyl aminopropyl carbodiimide, bis (imidoester), bis(succinimidyl ester) and diacid chloride.

10. The method for preparing a strip type optical biosensor according to claim 6, wherein the porous support is one or more selected from a group consisting of silica, alumina, niobium, tantalum, zirconium, titanium and a vinyl polymer.

11. A method for preparing a strip type optical biosensor as claimed in claim 1, comprising a complex of a porous support and a chromogenic enzyme supported inside the pores of the porous support and an oxidase, said method comprising:
   (1) at least one of:
      (a) adsorbing the chromogenic enzyme inside the pores of the porous support to form a porous support-chromogenic enzyme complex,
      (b) adsorbing the chromogenic enzyme inside the pores of the porous support to form a chromogenic enzyme-adsorbed porous support, and forming a porous support-chromogenic enzyme complex by forming a crosslinkage between the porous support and the chromogenic enzyme by adding a crosslinking agent to the chromogenic enzyme-adsorbed porous support, and
      (c) immobilizing the chromogenic enzyme inside the pores of the porous support through covalent bonding to form a porous support-chromogenic enzyme complex;
   (2) coating the porous support-chromogenic enzyme complex on a medial portion of a porous sensor strip membrane;
   (3) drying the porous sensor strip membrane; and
   (4) coating the oxidase on the porous sensor strip membrane, arranged so that the chromogenic enzyme of the porous support-chromogenic enzyme complex and the oxidase will catalytically react with a target analyte to generate a chromogenic material in the porous support and produce a colorimetric signal from the chromogenic material in the porous support, and wherein the porous support retains the chromogenic material for optical analysis of said colorimetric signal, so that the chromogenic material remains in the pores of the porous support and is prevented from escaping from the porous support.

12. The method for preparing a strip type optical biosensor according to claim 11, wherein the oxidase is one or more selected from a group consisting of glucose oxidase, cholesterol oxidase, polyphenol oxidase, monoamine oxidase, xanthine oxidase, cytochrome oxidase, ascorbic acid oxidase and D-arabino-1,4-lactone oxidase.

13. The method for preparing a strip type optical biosensor according to claim 11, wherein the chromogenic enzyme is one or more selected from a group consisting of peroxidase, alkaline phosphatase, tyrosinase, laccase, acetylcholinesterase and β-galactosidase.

14. The method for preparing a strip type optical biosensor according to claim 11, wherein the crosslinking agent is one or more selected from a group consisting of glutaric dialdehyde, diisocyanate, dianhydride, diepoxide, dialdehyde, diimide, 1-ethyl-3-dimethyl aminopropyl carbodiimide, bis(imidoester), bis(succinimidyl ester) and diacid chloride.

15. The method for preparing a strip type optical biosensor according to claim 11, wherein the porous support is one or more selected from a group consisting of silica, alumina, niobium, tantalum, zirconium, titanium and a vinyl polymer.

16. A method for preparing a strip type optical biosensor as claimed in claim 1, comprising a complex of a porous support and an oxidase and a chromogenic enzyme supported inside the pores of the porous support, said method comprising:
  (1) at least one of:
    (a) adsorbing the oxidase and the chromogenic enzyme inside the pores of the porous support to form a porous support-oxidase-chromogenic enzyme complex,
    (b) adsorbing the oxidase and the chromogenic enzyme inside the pores of the porous support to form an enzyme-adsorbed porous support, and forming a porous support-oxidase-chromogenic enzyme complex by forming a crosslinkage between the oxidase molecules and the chromogenic enzyme molecules by adding a crosslinking agent to the enzyme-adsorbed porous support, and
    (c) immobilizing the oxidase and the chromogenic enzyme inside the pores of the porous support through covalent bonding to form a porous support-oxidase-chromogenic enzyme complex;
  (2) coating the porous support-oxidase-chromogenic enzyme complex on a medial portion of a porous sensor strip membrane, arranged so that the oxidase and the chromogenic enzyme of the porous support-oxidase-chromogenic enzyme complex will catalytically react with a target analyte to generate a chromogenic material in the porous support and produce a colorimetric signal from the chromogenic material in the porous support, and wherein the porous support retains the chromogenic material for optical analysis of said colorimetric signal, so that the chromogenic material remains in the pores of the porous support and is prevented from escaping from the porous support.

17. The method for preparing a strip type optical biosensor according to claim 16, wherein the oxidase is one or more selected from a group consisting of glucose oxidase, cholesterol oxidase, polyphenol oxidase, monoamine oxidase, xanthine oxidase, cytochrome oxidase, ascorbic acid oxidase and D-arabino-1,4-lactone oxidase.

18. The method for preparing a strip type optical biosensor according to claim 16, wherein the chromogenic enzyme is one or more selected from a group consisting of peroxidase, alkaline phosphatase, tyrosinase, laccase, acetylcholinesterase and β-galactosidase.

19. The method for preparing a strip type optical biosensor according to claim 16, wherein the crosslinking agent is one or more selected from a group consisting of glutaric dialdehyde, diisocyanate, dianhydride, diepoxide, dialdehyde, diimide, 1-ethyl-3-dimethyl aminopropyl carbodiimide, bis(imidoester), bis(succinimidyl ester) and diacid chloride.

20. The method for preparing a strip type optical biosensor according to claim 16, wherein the porous support is one or more selected from a group consisting of silica, alumina, niobium, tantalum, zirconium, titanium and a vinyl polymer.

21. The method for preparing a strip type optical biosensor according to claim 16, wherein a ratio of the oxidase to the chromogenic enzyme is from 1:9 to 9:1.

22. The method for preparing a strip type optical biosensor according to claim 21, wherein, when the oxidase is glucose oxidase and the chromogenic enzyme is horseradish peroxidase, a ratio of the glucose oxidase to the horseradish peroxidase is from 2:8 to 4:6.

* * * * *

UNITED STATES PATENT AND TRADEMARK OFFICE
CERTIFICATE OF CORRECTION

PATENT NO. : 9,903,856 B2
APPLICATION NO. : 14/403240
DATED : February 27, 2018
INVENTOR(S) : Jungbae Kim It is certified that error appears in the above-identified patent and that said Letters Patent is hereby corrected as shown below:

In the Specification

Column 2, Line 54: "ah" should be -- an --.

Column 5, Line 2: "sopped" should be -- support --.

Column 6, Line 36: "Cholesterol-4-ene-3-one" should be -- Cholest-4-ene-3-one --.

Column 7, Lines 1-10: the "—" joining the ammonium nitrogen atom "⁺N" to the adjacent aromatic ring should be a -- = --.

Column 9, Line 18: "add" should be -- acid --.

Column 9, Line 51: "info" should be -- into --.

Column 10, Line 51: "glufaric" should be -- glutaric --.

Column 11, Line 18: "FIG. 8" should be -- FIG. 6 --.

Column 11, Line 53: "measurement 20" should be -- measurement. 20 --.

Column 11, Line 57: "faking" should be -- taking --.

Signed and Sealed this
Thirtieth Day of October, 2018

Andrei Iancu
*Director of the United States Patent and Trademark Office*